(12) United States Patent
Glunz et al.

(10) Patent No.: US 9,778,033 B2
(45) Date of Patent: Oct. 3, 2017

(54) DEVICE FOR PLACING A STOPPER WHILE SIMULTANEOUSLY CHECKING THAT THE STOPPER IS CORRECTLY POSITIONED

(71) Applicant: ARZNEIMITTEL GMBH APOTHEKER VETTER & CO. RAVENSBURG, Ravensburg (DE)

(72) Inventors: Alexander Glunz, Ravensburg (DE); Arno Schroff, Deggenhausertal (DE)

(73) Assignee: ARNEIMITTEL GMBH APOTHEKER VETTER & CO. RAVENSBURGH, Ravensburg (DE)

( * ) Notice: Subject to any disclaimer, the term of this patent is extended or adjusted under 35 U.S.C. 154(b) by 523 days.

(21) Appl. No.: 14/336,342

(22) Filed: Jul. 21, 2014

(65) Prior Publication Data

US 2014/0326040 A1    Nov. 6, 2014

Related U.S. Application Data

(63) Continuation of application No. 12/997,147, filed as application No. PCT/EP2009/004133 on Jun. 9, 2009, now Pat. No. 8,783,093.

(30) Foreign Application Priority Data

Jun. 12, 2008 (DE) ......................... 10 2008 030 038

(51) Int. Cl.
  *G01B 21/24*   (2006.01)
  *A61M 5/178*   (2006.01)
  *A61M 5/24*    (2006.01)
  *A61M 5/315*   (2006.01)
  *G01M 3/32*    (2006.01)

(52) U.S. Cl.
  CPC ............ *G01B 21/24* (2013.01); *A61M 5/1782* (2013.01); *A61M 5/24* (2013.01); *A61M 5/31515* (2013.01); *G01M 3/3236* (2013.01); *A61M 2005/2462* (2013.01)

(58) Field of Classification Search
  CPC ... G01B 21/24; G01M 3/3236; A61M 5/1782; A61M 5/31515; A61M 2005/2462
  USPC ............. 73/49.2, 49.3, 49.8; 141/7, 65, 192; 53/109; 220/315
  See application file for complete search history.

(56) References Cited

U.S. PATENT DOCUMENTS

| | | | | |
|---|---|---|---|---|
| 4,501,306 A | * | 2/1985 | Chu ........................ | B65B 3/003 141/192 |
| 4,811,252 A | * | 3/1989 | Furuse ................. | G01M 3/3263 702/51 |
| 6,199,350 B1 | * | 3/2001 | Brechel ................... | B65B 59/00 53/109 |

(Continued)

*Primary Examiner* — Harshad R Patel
*Assistant Examiner* — Suman K Nath
(74) *Attorney, Agent, or Firm* — Stephen T. Olson; Harness, Dickey & Pierce, P.L.C.

(57) ABSTRACT

A device places a plug and simultaneously checks a correct position alignment of the plug with a holding element for fixing a hollow body. The device has at least one first and one second opening and a plug placement mechanism with which the plug is be inserted into the second opening of the hollow body. The device has a measuring head that is traversed by at least one channel. The channel can be fluidically connected to the first opening of the hollow body. The device can further include a pressure sensor which can be fluidically connected to the channel of the measuring head.

18 Claims, 4 Drawing Sheets

(56) References Cited

U.S. PATENT DOCUMENTS

| | | | |
|---|---|---|---|
| 2003/0100866 A1* | 5/2003 | Reynolds | A61J 1/062 604/187 |
| 2007/0267092 A1* | 11/2007 | Rink | B65B 3/003 141/65 |
| 2008/0035233 A1* | 2/2008 | Luthi | B65B 3/003 141/7 |
| 2009/0241644 A1* | 10/2009 | Bonfiglioli | G01M 3/329 73/49.3 |

* cited by examiner

DEVICE FOR PLACING A STOPPER WHILE SIMULTANEOUSLY CHECKING THAT THE STOPPER IS CORRECTLY POSITIONED

CROSS-REFERENCE TO RELATED APPLICATIONS

This application is a continuation of U.S. patent application Ser. No. 12/997,147 filed on 9 Dec. 2010, which is a 371 U.S. National Stage of International Application No. PCT/EP2009/004133, filed 9 Jun. 2009, which claims priority to German Patent Application No. 10 2008 030 038.1, filed 12 Jun. 2008. The above applications are herein expressly incorporated by reference.

FIELD

The present disclosure relates to a device for placing a stopper while simultaneously checking that the stopper is correctly positioned.

DISCUSSION

The invention relates to a device for placing a plug while simultaneously checking a correct position alignment of the plug, moreover a device for checking a correct position alignment of a plug, a method for placing a plug while simultaneously checking a correct position alignment of the plug as well as a method for checking a correct position alignment of a plug.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
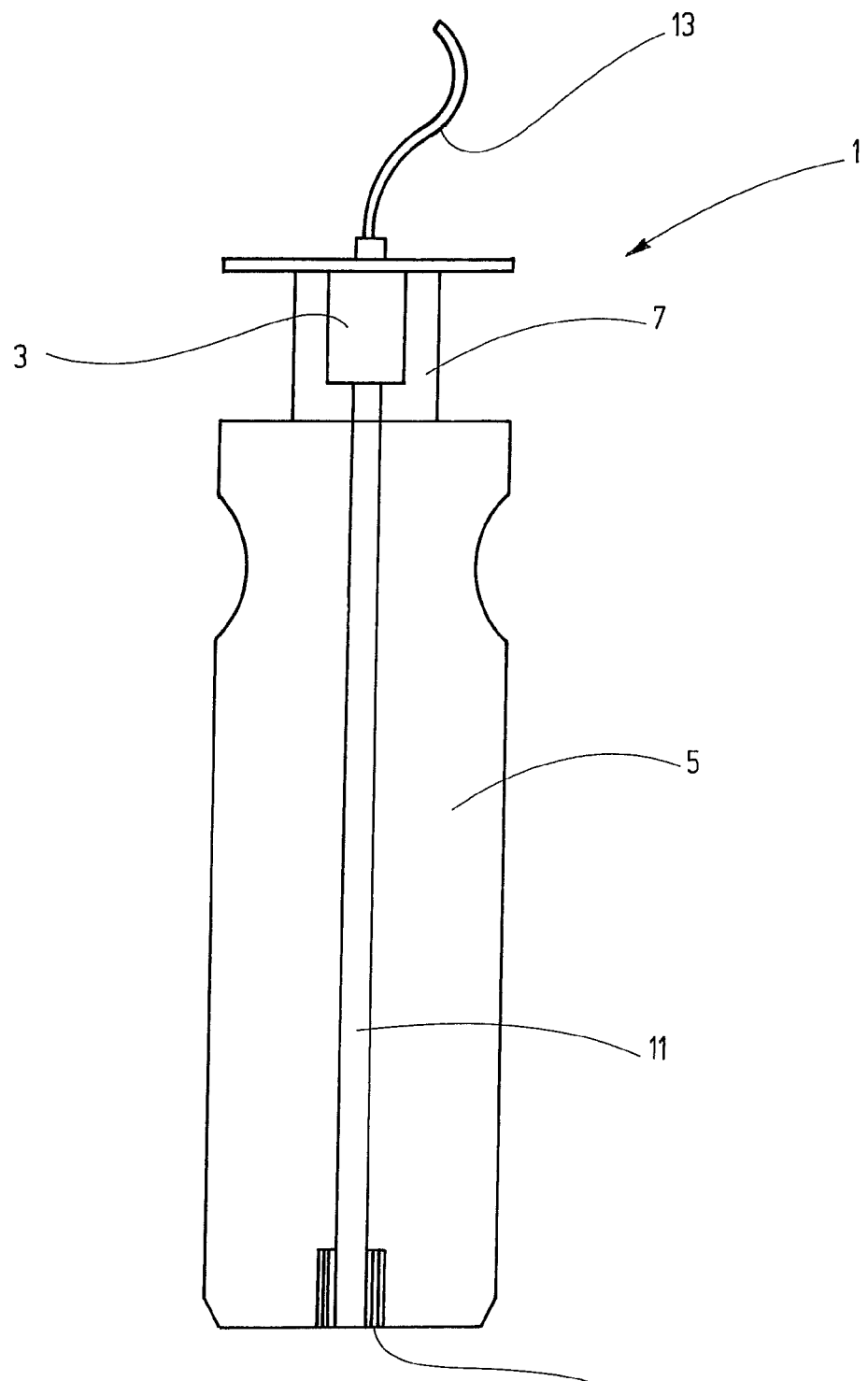
FIG. 1 is a diagrammatic view of a part of the device according to the present teachings.

Example embodiments will now be described more fully with reference to the accompanying drawings.

Devices of the referenced type are known. They comprise a holding element with which a hollow body, for example, a syringe or carpule, can be fixed. The hollow body thereby has at least one first and one second opening. A plug placement means is provided, which is used to insert a plug into the second opening of the hollow body. The hollow body typically comprises a cylindrical interior into which the essentially cylindrical plug is to be inserted through the second opening. If the longitudinal axes of the hollow body and the plug are aligned to one another correctly, the essentially cylindrical external surface of the plug bears against the typically cylindrical inner surface of the hollow body so that a sealing effect is produced, wherein the second opening of the hollow body is tightly closed by the plug. However, the error can occur during the placement of the plug that the plug placement means does not insert the plug into the second opening of the hollow body in the correct axial alignment. The essentially cylindrical plug is then rotated about an axis with regard to the longitudinal axis of the hollow body, which axis is perpendicular to its longitudinal axis as well as to the longitudinal axis of the hollow body. The result of this is that the essentially cylindrical circumferential surface of the plug does not bear or does not completely bear against the typically cylindrical inner surface of the hollow body, so that there is a reduced sealing effect or even no sealing effect here. If therefore the plug has a position alignment that is not correct in this respect, the second opening of the hollow body is not tightly closed. It can also occur that due to an error the plug placement means does not insert a plug into the second opening of the hollow body. Of course the second opening of the hollow body is not tightly closed in this case, either.

After the insertion of the plug into the second opening of the hollow body through the first opening of the same, a medium, for example, a pharmaceutical substance, is usually inserted. The plug then among other things should prevent this medium from being able to leak out through the second opening of the hollow body. However, if the plug has an incorrect position alignment or if no plug at all is present, if therefore the second opening of the hollow body is not tightly closed, the medium can leak out here and for example, contaminate a filling station or an entire production line that comprises at least one plug placement station and preferably one filling station. Typically, the media to be inserted into the hollow body are very expensive, so that losses due to incorrectly aligned or missing plugs are to be avoided.

In order therefore to be able to check the position alignment or the presence of the plug in the hollow body, known devices typically comprise at least one camera, which supplies pictures of the hollow body to an evaluation system. This system evaluates the images in general in a software-assisted manner in order to establish whether the plug was aligned correctly. Systems are also known that comprise optical wave guides, wherein a light beam is sent through the part of the hollow body in which the plug should correctly be arranged. A light measuring device, for example, a photodiode, is provided on the side of the hollow body opposite the optical wave guide, which light measuring device essentially detects whether a light beam traverses the hollow body. In this manner it can be established whether the plug is arranged in the hollow body at all.

Camera systems have the disadvantage of being very expensive and of requiring a complex and error-prone evaluation software. However, the actual alignment of a plug can be detected with them. In contrast, fiber optic systems are constructed much more simply and are therefore more cost-effective; they do not need any particularly complicated evaluation or control software, either. However, with their aid it is possible to detect only whether a plug has been inserted into the hollow body at all. The correct position alignment compared to the hollow body cannot be determined because the light beam used for testing can also be blocked out by a plug that was inserted into the hollow body twisted about an axis perpendicular to its longitudinal axis.

The object of the present invention is therefore to create a device that does not have the cited disadvantages in order to avoid as far as possible accidental filling of hollow bodies with plugs placed incorrectly or not at all.

The object on which the invention is based is attained by a device with a measuring head that is traversed by at least one channel, wherein the channel can be fluidically connected to the first opening of the hollow body. Furthermore, the device comprises a pressure sensor, which can be fluidically connected to the channel of the measuring head. In this manner the pressure sensor is also fluidically connected to the first opening of the hollow body. A pressure prevailing in the interior of the hollow body can therefore be detected by the pressure sensor. In particular, an overpressure in the interior of the hollow body can be detected, whereby it can be established whether the plug is aligned correctly in the hollow body. As already stated, a correctly aligned plug seals the second opening of the hollow body. If the plug is inserted into the second opening by the plug placement means, the gas volume in the interior of the hollow body is compressed at the same time. In this manner the internal pressure in the hollow body is increased, wherein the pressure in the at least one channel of the measuring head and thus also in the region of the pressure sensor is also increased, because these elements are fluidically connected to the first opening of the hollow body. During placement of the plug by the plug placement means an overpressure that can be measured by the pressure sensor is thus produced when the plug is aligned correctly. However, if the plug does not have a correct position alignment, if it is therefore twisted, it cannot close the second opening of the hollow body tightly. Accordingly, during the placement of the plug air can leak out of the interior of the hollow body through the second opening so that at least a slight overpressure can be detected on the pressure sensor. If the plug is missing completely, the second opening of the hollow body remains completely open during a plug placement cycle of the plug placement means so that no increased pressure can be detected at the pressure sensor.

A device is preferred that is characterized in that a pressure source is provided that can be fluidically connected to the first opening of the hollow body. With the aid of the pressure source a medium, for example, an inert gas or air, can be inserted into the hollow body. Preferably, an external pressure source is provided, that can preferably introduce the medium—preferably a specific volume of the medium—through the channel of the measuring head into the hollow body. The medium introduced into the hollow body by the pressure source increases, in addition to the compression due the placement of the plug, the internal pressure in the hollow body so that an over pressure is produced, which depends on the alignment of the plug. Here too a higher overpressure is regularly achieved when the plug is located in its correct position alignment, than when the plug is twisted or not present.

Further preferred exemplary embodiments are shown by the subordinate claims.

It is also the object of the invention to create a device for checking a correct position alignment of a plug, which can be carried out following the insertion of the plug into the hollow body in a separate step and optionally in a separate region of the production line. Also in this case the correct position alignment of the plug should be tested before the insertion of a preferably pharmaceutical substance into the hollow body.

The object is attained by a device with a holding element for fixing a hollow body, a measuring head, which is traversed by at least one channel, wherein the channel can be fluidically connected to a first opening of the hollow body. However, a plug is already inserted into a second opening of the hollow body, because here the test step is to be carried out separately from the placement of the plug. A pressure sensor is also provided, which can be fluidically connected to the channel of the measuring head. The device is characterized in that a pressure source is provided that can be fluidically connected to the first opening of the hollow body. Through the pressure source a preferably predetermined volume of a medium, for example, an inert gas or air, can be introduced into the interior of the hollow body so that an overpressure detectable at the pressure sensor is produced there when the plug is aligned correctly and thus tightly closes the second opening of the hollow body. However, if the plug is not correctly aligned, that is, twisted, it cannot tightly seal the second opening, so that here at least a part of the medium introduced into the hollow body by the pressure source can escape. Thus at least a lower overpressure is formed than is the case when the plug is correctly aligned. Where applicable, it is possible that no overpressure is formed. In particular if in the preceding plug placement cycle no plug was placed, no overpressure can form either because the second opening of the hollow body is completely open. It is therefore possible to establish based on the pressure detected at the pressure sensor whether the plug is aligned correctly in the hollow body or if a plug is present at all.

Through the detection of the pressure prevailing at the pressure sensor, accepted parts, that is, hollow bodies with correctly aligned plugs, can be very easily distinguished from rejected parts, that is, hollow bodies with twisted plugs or plugs not placed at all.

A device is preferred in which the holding element is enveloped by the measuring head. The holding element can thus be arranged on the measuring head, but it can also be a part of the measuring head. It is also possible for the measuring head as a whole to be embodied as a holding element. In this manner a particularly simple construction of the devices referenced here is possible.

A device is also preferred in which the plug is an end plug for a single-chamber carpule or a single-chamber syringe.

A device is also preferred in which the plug is a central plug for a dual-chamber or multi-chamber carpule or a dual-chamber or multi-chamber syringe.

Further advantageous embodiments are shown by the subordinate claims.

The object of the invention is furthermore to create a method through which a plug can be inserted into a hollow body, wherein the correct position alignment of the plug can be checked at the same time.

The object is attained through a method in which a hollow body is held with the aid of a holding element. A fluid connection between a channel traversing a measuring head and a pressure sensor is provided. Moreover, a fluid connection between the channel and a first opening of the hollow body is provided. In all this produces a fluid connection between the first opening of the hollow body—that is, also between an interior of the hollow body—and the pressure sensor. A plug is inserted into a second opening of the hollow body, wherein a pressure that can be detected at the pressure sensor is detected during the insertion of a plug. If the plug is correct aligned during insertion, a higher pressure can be detected at the pressure sensor than is the case with a twisted or missing plug. It is therefore very easily possible to establish based on the pressure measurement whether a plug is present and correctly aligned.

A method is preferred in which in addition a fluid connection between a pressure source and the first opening of the hollow body is provided. This takes place before the introduction of the plug. During the insertion of the plug a predetermined volume of a medium, for example, an inert gas or air, is then introduced into the first opening of the hollow body with the aid of the pressure source. An overpressure that can be detected at the pressure sensor is thus produced here on the one hand through the compression of the volume in the interior of the hollow body, and on the other hand through the additional insertion of a predetermined volume of a medium by the pressure source, if the plug is correctly aligned. However, if the plug is twisted or not present at all, a smaller overpressure or no overpressure at all forms, which can also be detected by the pressure sensor.

It is furthermore the object of the invention to create a method with the aid of which a correct position alignment of a plug can be checked after the plug has been inserted into a hollow body.

The object is attained through a method in which a hollow body is held with the aid of a holding element. A fluid connection between a channel traversing a measuring head and a pressure sensor is provided. Moreover, a fluid connection is provided between the channel and a first opening of the hollow body so that in all there is a fluid connection between the first opening of the hollow body—that is, also an interior of the hollow body—and the pressure sensor. In this exemplary embodiment a plug has already been placed into a second opening of the hollow body, because the check is to be carried out after the insertion of the plug. A fluid connection is provided between a pressure source and the first opening of the hollow body. A predetermined volume of a medium, for example, an inert gas or air, is introduced into the first opening of the hollow body with the aid of the pressure source, while the pressure that is detectable at the pressure sensor is detected. It is also obvious in this case that with a correctly embodied plug a higher overpressure can form in the interior of the hollow body, which then can also be detected by the pressure sensor, because it is in fluid connection with the interior. However, if the plug is twisted or not present, only a lower overpressure or no overpressure at all can form, which can also be detected by means of the pressure sensor. Therefore a conclusion can also be drawn here via the pressure measurement on whether a plug is present in the hollow body and is aligned correctly.

FIG. 1 shows a part of a device 1, with the aid of which a correct position alignment of a plug (not shown) into a hollow body (likewise not shown) can be checked.

The device 1 comprises a pressure sensor 3 and a measuring head 5. The pressure sensor 3 is connected to the measuring head 5 via a connecting adapter 7. A connecting adapter 7 is thereby only a connecting means that is particularly easy to realize between the pressure sensor 3 and the measuring head 5. It is also possible, for example, to provide a hose connection on the measuring head 5, which hose connection is connected to a hose. This hose can be connected, for example, via a further hose connection to the pressure sensor 3. It is important only that the pressure sensor 3 is in fluid connection with the measuring head 5 so that a pressure present in the measuring head 5 can be transferred to the pressure sensor 3.

At its lower end—seen from the observer's perspective—the measuring head 5 preferably has a sealing element 9 that is used for a pressure-tight fluid connection of a first opening of a hollow body (not shown) with the measuring head 5. The hollow body thereby typically has a head that comprises the first opening and the diameter of which is smaller than the outer diameter of the sealing element 9. With a flat bearing of the head of the hollow body on the lower side—seen from the observer's perspective—of the sealing element 9 with the application of a certain force the sealing element 9 is compressed and thus bears against the head of the hollow body in a sealing manner. An interior of the hollow body is then via the first opening in tight fluid connection with the measuring head 5.

At least one channel 11 traverses the measuring head 5 and optionally also the connecting adapter 7, so that the channel 11 is in fluid connection with the first opening and thus also with the interior of the hollow body as well as also in fluid connection with the pressure sensor 3. In this manner an overpressure prevailing in the interior of the hollow body can be measured by the pressure sensor 3. A cable 13 is preferably provided on the pressure sensor, by means of which cable a signal representing the measured pressure can be forwarded to a control device (not shown), in which the pressure prevailing at the pressure sensor 3 can be registered.

In the exemplary embodiment shown, the measuring head 5 is embodied as a holding element, which fixes the hollow body at least in the axial direction and into which the forces produced during the insertion of the plug can be conducted.

Figure 2:
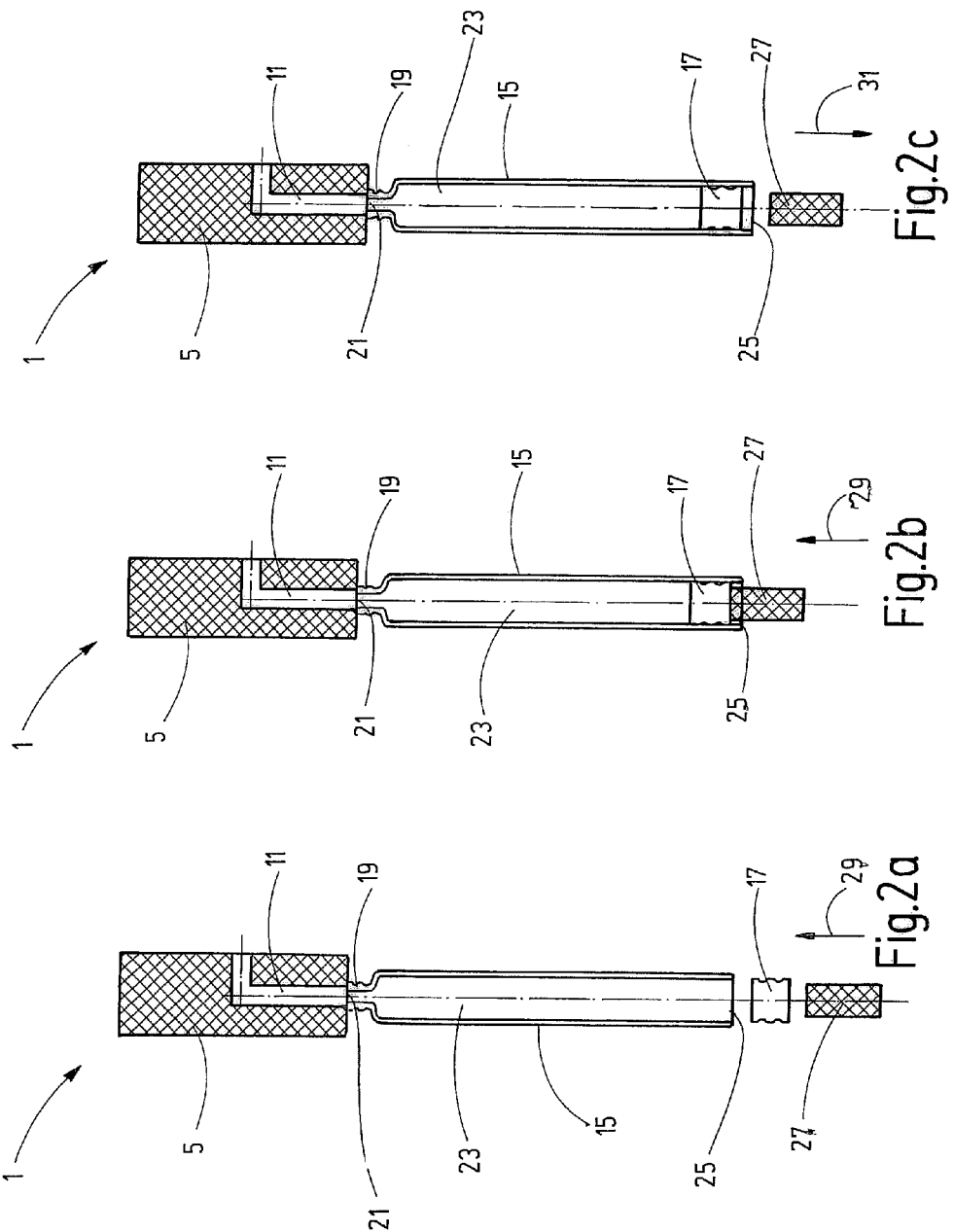
FIG. 2a is the device according to the present teachings before the insertion of the plug into the hollow body.
FIG. 2b is the device according to the present teachings during the insertion of the plug into the hollow body.
FIG. 2c is the device according to the present teachings after the insertion of the plug into the hollow body.

FIG. 2 shows a diagrammatic overview of the placement of a plug with the aid of a device 1. Identical elements and elements with the same function are provided with the same reference numbers so that in this respect we refer to the above description.

FIG. 2a shows the measuring head 5, which is traversed here by an angled channel 11. The connecting adapter 7 and the pressure sensor 3 are not shown.

The representation selected here is purely diagrammatic. It is not necessary for the pressure sensor 3 and the measuring head 5 to be embodied as separate parts. In particular the pressure sensor 3 and the measuring head 5 can be embodied in an integral manner so that preferably the measuring head 5 comprises the pressure sensor 3. In the exemplary embodiment shown, the measuring head 5 is embodied as a holding element, wherein it is used in particular as an abutment for a hollow body 15. During the insertion of a plug 17, the hollow body 15 bears with its head 19 flat against the measuring head 5, optionally in particular against the sealing element 9, not shown here.

It is clear from FIG. 2a that the channel 11 traversing the measuring head 5 is in fluid connection with a first opening 21 of the hollow body 15. It is thereby also in fluid connection with an interior 23 of the hollow body 15. Since the pressure sensor 3 (not shown) is in fluid connection with the channel 11 of the measuring head 5, connected thereby, it is also in fluid connection with the first opening 21 or the interior 23 of the hollow body 15. A pressure prevailing in the interior 23 can thus be detected by the pressure sensor 3.

The hollow body 15 has a second opening 25 at its end lying opposite the head 19 or the first opening 21—seen in the axial direction. The plug 17 can be inserted into this second opening with the aid of a plug placement means 27, which is indicated here by an arrow 29. The plug 17 is thus conveyed to the hollow body 15 from the side lying opposite the measuring head 5. Forces are hereby introduced into the hollow body 15, which act in the direction of the measuring head 5 and are absorbed thereby.

The plug 17 preferably has projections at its circumferential surface, which projections during the insertion of the plug 17 into the hollow body 15—seen in the radial direction—are compressed and thus contribute to an improved sealing effect, but on the other hand also minimize the friction of the plug 17 on an inner wall of the hollow body 15, because between them—seen in the axial direction—regions are arranged which do not bear against the inner wall.

The mode of operation of the device and method of the present teachings are explained in more detail below based on FIGS. 2b and 2c. Identical elements and elements with the same function are provided with the same reference numbers so that in this respect we refer to the description above.

In the exemplary embodiment shown or the embodiment of the method shown, the hollow body 15 is held with the aid of the measuring head 5 embodied as a holding element. As already stated, the plug 17 is inserted by the plug placement means 27 into the second opening 25 of the hollow body 15. During the insertion of the plug 17 into the hollow body 15, the medium held by the interior 23, typically air or an inert gas, is compressed because the volume available for it is reduced. An overpressure is produced hereby, which is transferred via the channel 11 and optionally the connecting adapter 7 to the pressure sensor 3. The pressure sensor detects the overpressure and generates a signal that is preferably forwarded via the cable 13 to the control device (not shown). The control device registers the pressure that prevails at the pressure sensor 3 while the plug 17 is inserted into the hollow body 15.

FIG. 2c shows the device 1 immediately after the insertion of the plug 17 into the hollow body 15. Identical elements and elements with the same function are provided with the same reference numbers so that in this respect we refer to the description above. The plug placement means 27 is now withdrawn again in the direction of an arrow 31 from the plug 17 or the hollow body 15 in order to release the hollow body 15.

Thereafter the hollow body 15 with the placed plug 17 is removed from the region of the device 1 and a new hollow body 15 with the plug 17 not yet placed is brought into active connection with the device 1. The positioning of the plugs 17 therefore necessary runs in a synchronized manner.

The control device also registers a pressure prevailing at the pressure sensor 3 when no plug 17 is inserted into a hollow body 15. Thus two pressures are registered by the control device during two phases of the machine cycle: preferably the maximum pressure is registered that is produced during the insertion of the plug 17 into the hollow body 15, and in a second phase of the cycle a pressure is registered that prevails at the pressure sensor 3 when no plug is inserted into the hollow body 15, preferably while no hollow body 15 is in active connection with the measuring head 5. The term active connection here indicates that the hollow body 15 bears with its head 19 against the measuring head 5, wherein there is a fluid connection between the first opening 21 and the channel 11.

In connection with the fluid connections mentioned here, it is obvious to one skilled in the art that they should preferably be embodied to be tight. Otherwise, it is namely impossible or possible only with difficulty to measure at the pressure sensor 3 the pressure that prevails in the interior 23 of the hollow body 15. On the other hand, minor leaks are not necessary a problem as long as at least a change in the pressure prevailing in the interior 23 during the insertion of the plug 17 and/or during the insertion of a predetermined volume of a medium with the aid of a pressure source—such as can be measured, for example, in an exemplary embodiment of the device 1 according to an embodiment of the method is measurable.

Preferably, the pressure sensor 3 detects the entire pressure pattern at least during the duration of the test cycle, that is, during the insertion of a plug 17 and/or during the insertion of a predetermined volume of a medium with the aid of the pressure source into the interior 23.

This pressure pattern is then forwarded for evaluation to the control device, optionally via a cable 13 or preferably also wirelessly, for example, via a Bluetooth or infrared interface.

The control device then evaluates the pressure pattern in that, for example, the maximum pressure is determined. If the pressure pattern has already been registered a sufficient time before the test cycle, a reference pressure can also be determined as a baseline from the pattern. It is therefore not absolutely necessary that a reference pressure prevailing at the pressure sensor 3 before the insertion of the plug 17 or before the insertion of a preferably predetermined volume of a medium is registered separately in the control device and that the pressure during the insertion of the plug or during the insertion of the predetermined volume of a medium is registered in the control device separately herefrom, instead the control device can plot a complete pressure pattern over a sufficient length of time and determine herefrom the maximum value relevant for the check as well as the reference value as a baseline.

In a preferred exemplary embodiment the control device forms the difference between the maximum pressure that prevails at the pressure sensor 3 while a plug 17 is inserted into the hollow body 15, and a pressure that prevails at the pressure sensor 3 while no plug 17 is inserted into the hollow body 15, preferably while no hollow body 15 is in active connection with the measuring head 5. It then compares the differential pressure determined with a preset desired value.

The desired value has been previously set such that it is adjusted to the concrete conditions of the production line. The desired value depends, for example, on the speed of the plug placement operation. It also depends on the start time, in particular on the phase position of the plug placement operation within the machine cycle. Moreover, the desired value depends on the region in which the plug 17 is positioned inside the hollow body 15. Namely, if the plug 17 is pushed further into the hollow body 15, this results in a greater compression of the medium contained in the hollow body 15 than when the plug is not inserted as far into the hollow body 15. Furthermore, the desired value also depends on the plug shape, in particular on the longitudinal extension of the plug 17, on the length of the hollow body 15 into which the plug is to be inserted, and on the diameter of the hollow body 15 into which the plug 17 is to be inserted.

The dependence on the speed of the plug placement operation indicates that an excessive pressure surge can rather be registered on the pressure sensor 3 with a quicker placement of the plug 17 than when the plug 17 is inserted into the hollow body 15 more slowly. Also the pressure can balance out via possibly existing residual leaks with a slow insertion of the plug 17, rather than with a quick plug placement operation.

The dependence of the phase position of the plug placement within the machine cycle indicates that the pressure measurement must be carried out in-phase, because otherwise irrelevant and completely meaningless pressure values may be registered which do not reflect the placement of the plug 17 due to an incorrect phase position. The pressure should thus be registered as far as possible as a maximum pressure that prevails in the test system when the plug 17 just reaches it end position.

The other referenced dependences directly indicate the volume difference that is produced during the operation of plug placement. It is directly understandable that a larger volume difference leads to a higher overpressure, while a smaller volume difference results in a smaller overpressure.

It is important that the desired value is determined such that it is adjusted to the conditions concretely prevailing in the production line. If the cited conditions are summarized in general under the term test conditions, the desired value must therefore be adjustable to different test conditions.

Figure 3:
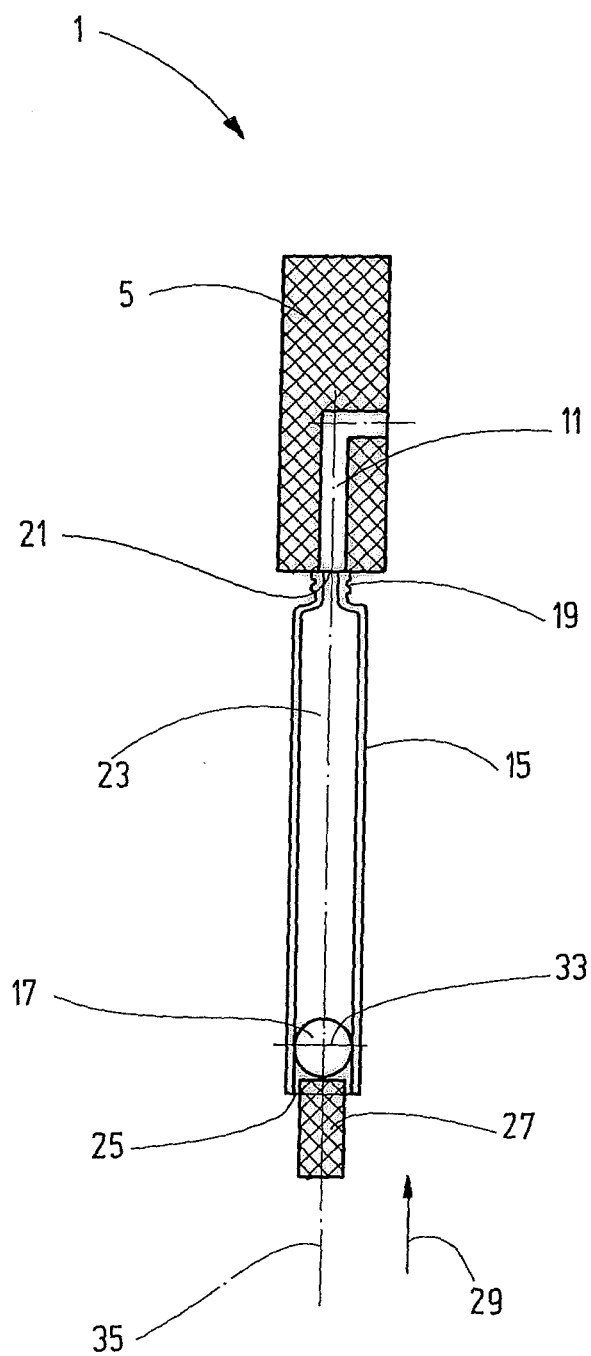
FIG. 3 is the device according to the present teachings during the insertion of an incorrectly aligned plug into the hollow body.

FIG. 3 shows a section of the plug placement and checking operation in which, as in FIG. 2b, a plug 17 is just being inserted into a hollow body 15 by a plug placement means 27. Identical elements and elements with the same function are provided with the same reference number so that in this respect we refer to the above description.

In contrast to FIG. 2b, however, the plug 17 in FIG. 3 is not correctly aligned, but it is twisted about an axis 33, which is perpendicular to its longitudinal axis and perpendicular to the longitudinal axis 35 of the hollow body 15, here by 90° by way of example. In this case, the longitudinal axis of the plug 17 is also perpendicular to the longitudinal axis 35 of the hollow body 15, while these axes are arranged parallel to one another with correct alignment of the plug 17.

It is obvious that with incorrect, that is, twisted alignment of the plug 17, the essentially cylindrical outer circumferential surface thereof cannot bear against an inner surface of the hollow body 15.

In any case, a twisted plug 17 is not able to seal the second opening 25, so that during the plug placement operation a reduced pressure can be detected at the pressure sensor 3. If the plug 17 is missing completely in the plug placement operation, no pressure increase at all can be detected at the pressure sensor 3.

A further exemplary embodiment of the device and the method is explained in more detail below in connection with FIG. 4. Identical elements and elements with the same function are provided with the same reference numbers so that in this respect we refer to the above description. In this exemplary embodiment a pressure source 37 is provided, which can introduce a medium into the hollow body 15, because it is in fluid connection with the first opening 21. For example, a branch from the channel 11 can be provided, which is fluidically connected to the preferably external pressure source 37. In this manner by means of the pressure source 37 a preferably preset volume of a medium, for example, an inert gas or air, can be introduced into the first opening 21 and thus the interior 23 of the hollow body, which leads to an increase in the pressure prevailing at the pressure sensor 3 precisely when a plug 17 is located in the hollow body 15. If conversely no plug 17 is located in the hollow body 15, the volume introduced therein is directly released into the environment, so that no pressure increase can take place. The pressure increase is necessarily higher when the plug 17 is correctly aligned and thus is arranged in the hollow body 15 in a sealing manner. If the plug were instead inserted into the hollow body in a twisted manner, gaps or leaks are present that prevent the buildup of a correspondingly high overpressure.

Figure 4:
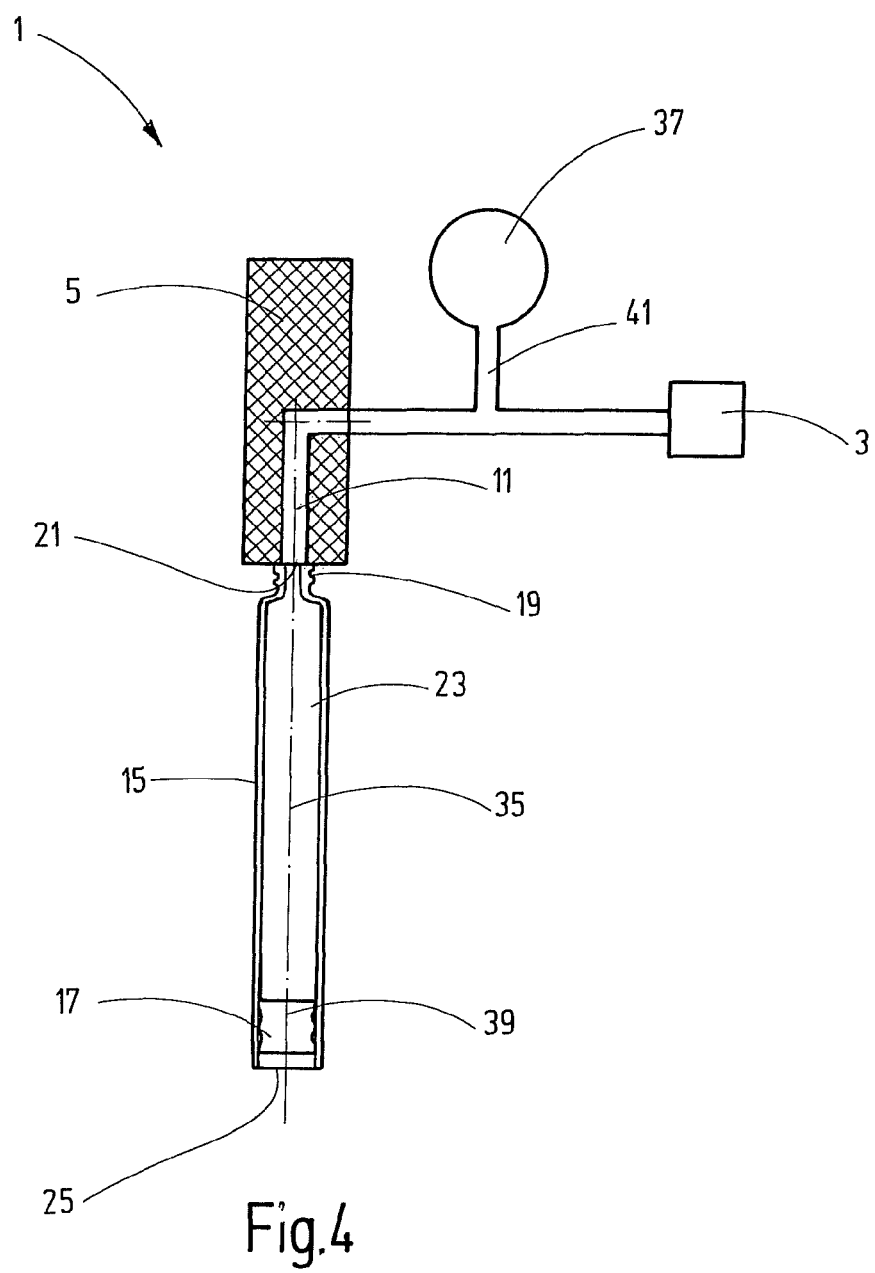
FIG. 4 is a diagrammatic view of a device according to the present teachings.

It is obvious that the exemplary embodiment of the device and the method shown diagrammatically in FIG. 4 serves a check of the correct alignment of the plug 17 in the hollow body 15 after the insertion of the plug 17 into the hollow body 15. Therefore here a separate test step is provided that can be carried out separately from the plug placement cycle of the production line. In particular, this test step can also be carried out in a spatially separate manner from the plug placement step so that it therefore take place in a separate device of the production line. Of course, it is also possible, however, to carry out the test step after the plug placement cycle only in terms of time, but in the same device 1.

A control device is also provided here that is used for the detection of a maximum pressure, which is produced when a preferably preset volume of a medium is introduced into the hollow body 15 by the pressure source 37. Preferably, the control device is also able to detect a reference pressure which prevails at the pressure sensor 3 when no volume of a medium is introduced into the hollow body 15 due to the pressure source 37, preferably when no hollow body 15 is in active connection with the measuring head 5.

In the exemplary embodiment shown in FIG. 4, the plug 17 is aligned correctly, its longitudinal axis 39 is therefore oriented parallel to the longitudinal axis 35 of the hollow body 15.

With regard to the control device or the pressure measurement and pressure registration, everything that has already been said in connection with FIG. 2 also applies in this exemplary embodiment. In particular, the control element can also here detect a complete pressure pattern at the pressure sensor and from this preferably determine a maximum pressure and optionally also a reference pressure as a baseline.

The control device can optionally compare the maximum pressure with a desired value or the difference of the registered maximum pressure and the reference pressure with a corresponding other desired value. This desired value, as described above, also depends on various test conditions and is preferably adaptable thereto.

The present exemplary embodiment is to be used for a separate check for hollow bodies 15 with plug 17 already placed. In this case, the maximum pressure produced or reference pressure essentially depends on the volume formed by the hollow body 15, the channel 11, optionally the connecting adapter 7 (not shown) or a corresponding connection hose or another connection means and the pressure sensor 3, as well as an additional channel or channel section 41 optionally connected to the pressure source 37.

In another preferred exemplary embodiment of the device and the method it is also possible to supplement the device shown in FIG. 2 by a pressure source 37. This pressure source is then likewise fluidically connected to the first opening 21 of the hollow body 15. It is therefore possible to introduce a preferably predetermined volume of a medium, for example, an inert gas or air, into the first opening 21 of the hollow body 15 and thus into the interior 23 thereof with the aid of the pressure source 37, while the plug 17 is inserted by the plug placement means 27 into the second opening 25 of the hollow body 15. In this case, a pressure increase can be registered at the pressure sensor 3 with a plug 17 generally present, which pressure increase is to be attributed on the one hand to the compression of the medium present in the interior 23 by the insertion of the plug 17, and on the other hand to the introduction of the preferably predetermined volume of another or the same medium by the pressure source 37. If the plug 17 is not correctly aligned, but it is twisted, this pressure increase is smaller than is the case with a correctly aligned plug 17. If optionally no plug 17 at all is present, depending on the geometric conditions, for example, the length of the hollow body 15 and the diameter of the second opening 25, only a very slight pressure increase or no pressure increase at all should be detectable at the pressure sensor 3. The evaluation of the pressure increase or pressure pattern or individual pressures detected during the process can be carried out in the control device in the manner already described. Of course, the check here in turn must be based on a different desired value that is adjusted to the concrete test conditions.

All of the exemplary embodiments and embodiments have in common that a pressure registered by the control device is compared to a desired value. If it reaches the desired value or at least falls within a predetermined tolerance range, the test specimen is evidently a hollow body 15 with a correctly placed plug 17, thus an accepted part. If, however, the registered pressure is substantially below the desired value, the plug 17 is evidently twisted or has not been placed at all. The test specimen is therefore a rejected part.

Typically, the placement of the plug 17 as well as the checking of its correct alignment are carried out in a production line. The production line comprises various stations, including a plug placement station and a test station, either comprised thereby or arranged separately, for checking the correct alignment of the plug 17. In the same production line, preferably a station can be integrated in which a medium, for example, a pharmaceutical substance, is introduced into the interior 23 of the hollow body 15. This substance is typically more expensive than the hollow body 15 and the plug 17. It must therefore be ensured that no losses of the substance occur because a plug 17 is not correctly aligned and the hollow body 15 for this reason is not tightly closed. Furthermore, the leakage of a substance this type through the second opening 25 not tightly closed can possibly lead to the entire production line being contaminated. In particular microbiological or hygienic problems can result here which in the worst case can lead to a total failure of the production line, wherein a complex and expensive decontamination and sterilization can be necessary.

It must therefore be avoided that the corresponding substance is introduced into rejected parts, that is, in hollow bodies 15 with incorrectly aligned or missing plugs 17.

To this end a control program is preferably provided in the control device, in which control program a marking can be placed internally, which is used to detect a rejected part. The marking can preferably be placed as a virtual mark in the control program. In another exemplary embodiment, however, it is also possible to attach the marking to the rejected part as a physical identifier, for example, as a sticker or in another manner. With the aid of the marking it can then be precisely determined which parts in the production line are rejected parts. The marking can be used to remove rejected parts immediately, or they can be passed through over the entire production line until at the end thereof the hollow bodies 15 with incorrectly aligned plugs 17, which are marked as rejected parts, are removed as waste. In particular the marking as a rejected part is passed on to the station within the production line that is used to fill a hollow body 15 with a medium, preferably a pharmaceutical substance. It can thus be avoided that hollow bodies with an incorrectly placed plug 17 or a plug not placed at all are filled with the substance. Hereby on the one hand the loss of in part very expensive pharmaceutical substance is avoided, on the other hand it is avoided that the pharmaceutical substance soils or contaminates the production line. In particular complex service work such as, for example, a decontamination or sterilization can thus also be reduced or even avoided completely.

In all of the described exemplary embodiments or embodiments, the device and the method are suitable for checking the correct alignment of a plug 17 in a hollow body 15 when this plug 17 is the first sealing element that is inserted into the second opening 25 of the hollow body 15. The result is that the plug 17 can be an end plug for a single-chamber carpule or a single-chamber syringe. The result is also, however, that the plug 17 can be a central plug for a multi-chamber carpule a dual-chamber carpule or a multi-chamber or dual-chamber syringe. This list is to be understood to be by way of example and not restricting. It is important that in principle the correct alignment of the plug 17 in the hollow body 15 can be checked as long as the plug 17 is the first sealing element that is inserted into the hollow body 15 through the second opening 25. In this manner an overpressure is produced in the interior 23 of the hollow body 15 during the insertion of the plug 17, which overpressure can be registered by the pressure sensor 3 through the first opening 21 lying opposite the plug 17. On the other hand, a pressure can also be introduced into the hollow body through the first opening 21, which pressure likewise can be detected by the pressure sensor 3.

All of this shows that all of the exemplary embodiments or embodiments of the proposed device and the proposed method in a very simple, less error-prone manner permit a quick, secure and easily reproducible checking of the correct alignment of a plug 17 in a hollow body 15. In particular, the proposed devices do not need expensive and complicated camera systems or likewise expensive and complicated image evaluation software, but they are nevertheless able not only to detect whether a plug 17 has been placed at all, but also to check whether the plug 17 is located in a correct alignment.

Further advantageous embodiments are shown by the subordinate claims.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for placing a plug in a hollow body while simultaneously checking a correct position alignment of the plug, the hollow body having at least one first opening and one second opening, the device comprising:
   a plug placement means for inserting the plug into the second opening of the hollow body;
   a measuring head traversed by at least one channel, the channel for fluid connection to the first opening of the hollow body; and
   a pressure sensor for checking the correct position alignment of the plug, and the pressure sensor fluidically connected to the channel of the measuring head.

2. The device according to claim 1, further comprising a pressure source fluidically connected to the first opening of the hollow body.

3. The device according to claim 1, wherein the plug is an end plug and the hollow body is embodied as a single-chamber carpule or syringe.

4. The device according to claim 1, further comprising a control device, in which the pressure prevailing at the pressure sensor can be registered.

5. The device according to claim 1, wherein the measuring head fixes the hollow body in at least an axial direction.

6. The device according to claim 1, wherein the pressure sensor is operative for detecting a prevailing pressure in an interior of the hollow body.

7. The device according to claim 1, wherein the measuring head and the pressure sensor are embodied in an integral manner.

8. A method for placing a plug in a hollow body while simultaneously checking a correct position alignment of the plug, the hollow body having at least one first opening and one second opening, the method comprising:
 holding the hollow body;
 providing respectively one fluid connection between a channel traversing a measuring head and a pressure sensor on one hand and the channel and a first opening of the hollow body on another hand;
 inserting the plug into a second opening of the hollow body; and
 detecting the pressure detectable at the pressure sensor during the insertion of the plug to check the correct position alignment of the plug.

9. The method according to claim 8, further comprising registering pressure values detected at the pressure sensor by a control device.

10. The method according to claim 9, further comprising:
 detecting a reference pressure prevailing at the pressure sensor before the insertion of the plug and registering this pressure in the control device;
 registering the pressure detected at the pressure sensor during the insertion of the plug in the control device;
 forming a differential pressure from the pressure measured during the insertion of the plug and the reference pressure measured before the insertion of the plug in the control device; and
 comparing the differential pressure with a preset value.

11. The method according to claim 8, further comprising marking the hollow body as a rejected part when the plug is not aligned correctly.

12. The method according to claim 8, further comprising introducing a medium into the first opening of the hollow body during the insertion of the plug.

13. The method according to claim 8, the method comprising:
 providing fluid connection between a pressure source and the first opening of the hollow body; and
 introducing a predetermined volume of a medium into the first opening of the hollow body with aid of the pressure source;
 wherein detecting the pressure detectable at the pressure sensor occurs during introduction of the volume of the medium into the first opening of the hollow body.

14. The method according to claim 13, wherein the measuring head is a holding element and wherein the method further comprises fixing the hollow body in at least an axial direction with the holding element.

15. The method according to claim 13, further comprising detecting a prevailing pressure in an interior of the hollow body with the pressure sensor.

16. The method according to claim 13, wherein providing fluid connection between the pressure source and the first opening of the hollow body occurs before insertion of the plug.

17. The method according to claim 13, wherein introducing the predetermined volume of the medium into the first opening of the hollow body with aid of the pressure source occurs during insertion of the plug.

18. The method according to claim 13, wherein:
 providing fluid connection between the pressure source and the first opening of the hollow body occurs before insertion of the plug; and
 introducing the predetermined volume of the medium into the first opening of the hollow body with aid of the pressure source occurs during insertion of the plug.

* * * * *